United States Patent [19]

Murib

[11] 4,107,204
[45] * Aug. 15, 1978

[54] CATALYTIC OXIDATION OF ACROLEIN TO ACRYLIC ACID

[75] Inventor: Jawad H. Murib, Cincinnati, Ohio

[73] Assignee: National Distillers and Chemical Corporation, New York, N.Y.

[*] Notice: The portion of the term of this patent subsequent to Sep. 27, 1994, has been disclaimed.

[21] Appl. No.: 805,048

[22] Filed: Jun. 9, 1977

Related U.S. Application Data

[63] Continuation-in-part of Ser. No. 603,907, Aug. 11, 1975, Pat. No. 4,051,181.

[51] Int. Cl.$^2$ .............................................. C07C 51/32
[52] U.S. Cl. .............................. 260/530 N; 252/443; 252/447; 252/460; 252/474; 260/531 R; 260/603 C
[58] Field of Search .................................. 260/530 N

[56] References Cited

U.S. PATENT DOCUMENTS

| 2,042,220 | 5/1936 | Groll et al. | 260/531 R |
| 3,647,867 | 5/1972 | Sennewald et al. | 260/531 R |
| 3,778,477 | 12/1973 | Muller et al. | 260/603 R |
| 4,051,181 | 9/1977 | Murib | 260/531 R |

Primary Examiner—Vivian Garner
Attorney, Agent, or Firm—Kenneth D. Tremain

[57] ABSTRACT

A three-step process for the production of acrolein and/or acrylic acid from propylene involves oxidizing the propylene in the presence of a palladium catalyst and acetic acid to produce allyl acetate, hydrolyzing the resulting allyl acetate to produce allyl alcohol and acetic acid, recycling the acetic acid produced to the propylene oxidation step, and oxidizing the allyl alcohol in the presence of a supported palladium-copper or palladium-silver metal catalyst. The acrolein and/or acrylic acid is produced in good yield at low temperatures. Acrylic acid is also produced in good yield at low temperatures by the catalytic oxidation of acrolein in the presence of the supported palladium-copper or palladium-silver metal catalyst.

8 Claims, No Drawings

CATALYTIC OXIDATION OF ACROLEIN TO ACRYLIC ACID

CROSS-REFERENCE TO RELATED APPLICATION

This application is a continuation-in-part of application Ser. No. 603,907, filed Aug. 11, 1975, now U.S. Pat. No. 4,051,181.

BACKGROUND OF THE INVENTION

In U.S. Pat. No. 3,792,086, a one-step process for the oxidation of propylene into acrylic acid at temperatures up to 300° C. is disclosed. The catalyst used in this process is a supported palladium metal, alone or admixed, alloyed or in solid solution with a minor amount of a further metal, e.g., a Group IB metal such as silver or gold, and phosphoric acid. The use of $H_3PO_4$ is essential in this process in order to obtain the desired results. Unfortunately, the use of the phosphoric acid has inherent disadvantages among which equipment corrosion encountered in feeding the acid to the reaction zone and deterioration of the silica and alumina catalyst supports by the acid can be mentioned.

I have now found that the use of $H_3PO_4$ can be avoided by converting propylene into acrylics by a multi-step route. In the first step, propylene is oxidized in the presence of a palladium metal catalyst and acetic acid to produce allyl acetate and water. In the second step, the allyl acetate is hydrolyzed in the presence of an acid catalyst to produce allyl alcohol and acetic acid.

The acetic acid produced in the second step is recycled for use in the propylene oxidation stage. The next step in my process involves the oxidation of the allyl alcohol in the presence of a supported palladium-copper or palladium-silver metal catalyst in the vapor phase and at low temperatures to produce acrolein and/or acrylic acid in good yield.

In McClain et al, U.S. Pat. No. 3,739,020, a vapor phase process for the preparation of carboxylic acids by the direct oxidation of 2-4 carbon atom alkanols in the presence of a solid palladium metal containing catalyst at temperatures up to 150° C. is disclosed. The palladium catalyst used in this process can be in admixture, alloyed or in solid solution with other metals such as, e.g., gold. The patent also teaches that the catalyst can additionally carry as a promoter, a compound of various metals including copper, most often in the oxide, carbonate or acetate form.

It is known to oxidize primary alcohols with air, oxygen or oxygen producing substances to produce the corresponding aldehydes or carboxylic acids. However, if unsaturated primary alcohols are involved, secondary reactions usually take place to a relatively great extent because the oxidizing agent also attacks the double bond and results in extensive decomposition of the molecule, producing, e.g., formaldehyde, glyoxal, formic acid or oxalic acid. Low yields are generally obtained because the carboxylic acids and aldehydes are very reactive compounds, which themselves are subject to addition reactions and particularly to polymerization. In U.S. Pat. No. 3,449,413, it is taught that these problems can be substantially overcome by carrying out the oxidation of the alcohols in an alkaline aqueous medium containing a mixture of cuprous oxide or cuprous hydroxide and a noble metal and/or its oxide or hydroxide.

The prior art also teaches that allyl alcohol can be oxidized to acrolein and/or acrylic acid at high temperatures using a copper or silver catalyst or palladium salts promoted with a combination of other metals. Thus, U.S. Pat. No. 2,042,220 teaches using a silver catalyst at temperatures from 360°–550° C.; CA 50, 11940 (1955) describes a silver catalyst at temperatures of 200°–400° C. with the best yield of acrolein being 53% at 340°–350° C.; CA 40, 4348 describes the use of a silver catalyst at 200°–240° C. with a conversion of 76% of theory; CA 63, 8184 teaches the production of acrolein using a silver or copper catalyst at 200°–530° C., the copper causing more of the allyl alcohol to burn into $CO_2$; and CA 70, 87049 teaches the use of a salt or coordination compound of palladium such as a mixture of palladium acetate, lithium acetate and cuprous acetate.

U.S. Pat. No. 3,862,236 teaches that allyl alcohol can be isomerized into propionaldehyde, a saturated aldehyde, by passing the allyl alcohol in the gas phase over a supported palladium and gold catalyst at a temperature of 50°–250° C.

Another aspect of the invention is the catalytic oxidation of acrolein to acrylic acid using a supported palladium-copper catalyst or palladium-silver catalyst. The art in U.S. Pat. Nos. 3,631,079 and 3,655,747 to Sennewald and Vogt shows that saturated aldehydes may be oxidized to carboxylic acids in the gas phase utilizing a catalyst containing palladium and an additional metal, of which numerous metals are disclosed, and further containing an alkali metal or alkaline earth metal compound as an activator. These patents are directed to saturated aldehydes such as acetaldehyde and the preferred catalyst composition contains palladium, gold and an activator such as potassium acetate. This catalyst composition is not suitable for the oxidation of acrolein to acrylic acid.

U.S. Pat. No. 3,456,002 to Komuro and Nagai discloses a process for oxidizing unsaturated aldehydes to the corresponding unsaturated acids using a catalyst consisting of vanadium oxide and antimony oxide. A similar process is disclosed in U.S. Pat. No. 3,646,127 to Akiyama et al. which employs a catalyst comprising (a) molybdenum, (b) palladium or platinum, (c) silver, thorium, antimony, bismuth, chromium, selenium or tellurium, and (d) oxygen, as the essential components. CA 79, 136525p (1973) describes the vapor phase oxidation of methacrolein to form methacrylic acid using a catalyst containing Pd-P-V-Mo-O. Similarly, CA 78, 57773u (1973) describes the catalytic oxidation of acrolein using a catalyst composed of Sb, Ni, Mo, Pd, and O.

Liquid phase oxidation of aldehydes is known. Ca 79, 78126w (1973) discloses the use of Pd black. U.S. Pat. No. 3,479,403 describes the oxidation of aldehydes using ruthenium under controlled electromotive potential oxidation conditions. CA 64, 6500 (1966) shows an aqueous treating solution containing Pd chloride, Li chloride, Li acetate, Cu acetate, acrolein, and acetic acid.

It is the object of this invention to provide a new process for the oxidation of allyl alcohol into acrylics and to provide a multi-step continuous process for converting propylene into acrylics which avoids the use of phosphoric acid, has lower heat requirements than prior art processes and provides high overall conversion and selectivity.

A further object of this invention is to provide a new process for the oxidation of acrolein to acrylic acid.

This and other objects of the invention will become apparent to those skilled in the art from the following detailed description.

SUMMARY OF THE INVENTION

This invention relates to a step-wise process for the oxidation of propylene into acrylics via allyl alcohol. More particularly, the invention concerns a multi-step process, which can be carried out continuously, in which propylene is oxidized to allyl acetate, the allyl acetate is hydrolyzed to allyl alcohol and acetic acid, the acetic acid is recycled to the propylene oxidation step, and the allyl alcohol is oxidized to acrylic acid and/or acrolein in good yield and at low temperatures.

In accordance with the present invention, propylene is oxidized in the presence of acetic acid to allyl acetate. The allyl acetate is then hydrolyzed, the resulting acetic acid being recycled to the propylene oxidation stage and the resulting allyl alcohol being oxidized in the presence of a palladium-copper or palladium-silver catalyst at low temperatures to produce acrolein and/or acrylic acid in good yield.

The steps of the present method can be shown by the following equations:

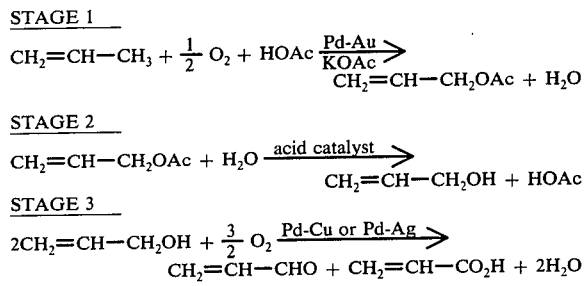

The oxidation of propylene in the presence of acetic acid and a palladium catalyst is known in the art. For example, it is described in U.S. Pat. No. 3,275,680. Similarly, the hydrolyzation of the allyl acetate is also known in the art and a description of this process can be found in German. Offen. No. 1,949,537.

At the end of the hydrolyzation step, the resulting allyl alcohol and acetic acid are separated by conventional processes known in the art. The acetic acid is then recycled to the propylene oxidation stage and the allyl alcohol is further oxidized in accordance with the present invention into acrylic acid and acrolein.

The oxygen feed employed in the instant process can be pure oxygen gas or, alternatively, an oxygen containing gas mixture such as air or air enriched with oxygen. The oxygen concentration is not critical, but generally the molar ratio of oxygen to allyl alcohol will range from about 1:1 up to about 15:1.

The catalyst used in this invention is a supported two-metal catalyst, one metal being palladium and the other metal being either copper or silver. The metals may be employed as a mixture, alloy or solid solution. Any of the conventional inert carriers or supports such as alumina, silica, silicon carbide, carbon, titania, zirconia, zeolites (molecular sieves) and the like can be used. The palladium metal is employed in amounts from about 0.01 to 5 weight percent, preferably from about 0.1 to 2 weight percent of the weight of the supported catalyst. The amount of copper or silver used is from about 0.001 to 10 weight percent, preferably about 0.05 to 3 weight percent, based on the total weight of the supported catalyst and the weight ratio of copper or silver to palladium is about 0.1 to 2.0 and preferably about 0.5 to 1.5. The supported catalyst can be prepared by any of the methods known in the art.

It has been found desirable in accordance with the present invention to additionally incorporate a protonated material, such as water vapor in the reaction mixture. The precise manner in which the steam influences the reaction is not presently understood and although water is a product of the oxidation reaction, it has been found that the presence of water in the reaction medium increases the reaction rate and improves the selectivity and conversion of allyl alcohol to the acrylic products. The steam is employed in an amount such that the molar ratio of water vapor to allyl alcohol is about 1:1 to 20:1 and preferably about 1:1 to 10:1.

The oxidation reaction is carried out in the vapor phase by passing the reaction mixture through the heated catalyst at a temperature of 125°–320° C., preferably from about 150°–200° C. The superficial contact time, i.e., calculated from space velocity and volumes, can be from 0.1 to 10 seconds and preferably is about 1 to 5 seconds. As a general rule, the reaction temperature employed varies inversely with the superficial contact time.

In preparing the reaction mixture, air or $O_2$ can be bubbled through liquid water and liquid allyl alcohol separately and the vapors combined and fed to the reactor, or the air or $O_2$ can be bubbled through an azeotropic mixture of water and allyl alcohol and the vapor fed to the reactor. Alternatively, the water and allyl alcohol can be vaporized separately and fed to the reactor. The reaction mixture can also, if desired, contain an inert gas such as nitrogen or carbon dioxide and gaseous acetic acid can also be used as an inert diluent, in an amount which can range up to 77%.

The concentration of allyl alcohol in the gaseous feed will generally be about 1–20%, preferably about 1–15% by volume. The composition of the gaseous feed will generally be chosen to be outside the flammability limits. The precise limits are a function not only of the amount of allyl alcohol and oxygen but also of the nature of the inert gas or diluent and its concentration and also the temperature and pressure. The pressure employed is not critical and can be from ambient up to 75 psia. It is preferred, however, to conduct the reaction at or about ambient pressure.

After completion of the oxidation reaction, the products can be recovered and separated in the conventional manner. For example, the reaction mixture can be condensed or scrubbed with water and the products isolated therefrom.

Another important aspect of the invention is the catalytic oxidation of acrolein to form acrylic acid. It has been found that the same supported two-metal catalyst composition as described hereinabove, to wit, one metal being palladium and the other metal being either copper or silver, provides good percent conversion and percent selectivity to acrylic acid when employed as the catalyst in the oxidation of acrolein. A catalyst containing palladium metal alone results in substantial combustion of the acrolein to carbon dioxide with only trace amounts of acrylic acid being formed. Substantially similar results are obtained when using palladium-gold metal catalyst compositions. A palladium-copper metal catalyst or a palladium-silver catalyst, however, provides good percent conversion and percent selectivity to acrylic acid from acrolein when employed in the process of the invention. The above description applies equally to the use of acrolein. Thus, the reactants (substituting acrolein for allyl alcohol), reactant concentrations, reaction conditions, catalyst compositions, etc., for this aspect of the invention are the same as described hereinabove for the allyl alcohol oxidation.

The following Examples serve to further illustrate the invention but are not intended to limit it. Throughout this specification and claims, all parts and percentages are by weight and all temperatures are in degrees Centigrade unless otherwise indicated. Further, as employed herein, the percent conversion and percent selectivity are defined as follows:

$$\% \text{ Conversion} = \frac{\text{Moles of allyl alcohol actually reacted}}{\text{Moles of allyl alcohol fed to reactor}} \times 100$$

$$\% \text{ Selectivity} = \frac{\text{Moles of Product}}{\text{Moles of allyl alcohol actually reacted}} \times 100$$

Similarly for % conversion and % selectivity of acrolein; acrolein being substituted for allyl alcohol in the above formulas.

EXAMPLE 1

A Pyrex glass reactor 12 cm × 2.5 cm outer diameter and provided with a thermowell as packed with 31 g (30 ml bulk volume) of a catalyst containing 2% palladium and 0.5% copper supported on alumina. The reactor was heated in an oil bath at 150°–155° C. A gaseous stream containing 1.4 mole percent allyl alcohol vapor, 12.8 mole percent steam and 85.8 mole percent air was passed through the heated reactor at a rate such that the superficial contact time was 1.5 seconds. Upon exiting the reactor, the reaction mixture was bubbled through two 40 ml water traps (0° C.) which were connected in series. The aqueous solution collected over a 1-hour period was then analyzed by gasliquid chromatography and alkaline titration. The analysis gave the following results:

|  | g./l. cat./hr. |
|---|---|
| Acrylic Acid | 12.3 |
| Acrolein | 26.9 |
| Propionic Acid | 1.4 |
| Propionaldehyde | 1.7 |
| Acetaldehyde | Trace |

These results, combined with the amount of $CO_2$ formed (10.4 g./l. cat./hour), showed that the conversion of allyl alcohol per single pass was 80% and the selectivity to the acroyl moiety was 83%. The acroyl molar distribution corresponded to 27.7% acrylic acid and 72.3% acrolein.

EXAMPLE 2

Example 1 was repeated except that the catalyst contained 2% palladium and 0.5% silver supported on alumina and the reactor temperature was 143° C. Analysis showed that the allyl alcohol was oxidized to the same products as in Example 1 with 79.5% conversion and 73.3% selectivity to the acroyl moiety. The acroyl molar distribution corresponded to 47% acrylic acid and 53% acrolein.

Oxidizing allyl alcohol with a catalyst of palladium alone leads to high combustion of the allyl alcohol. Incorporation of gold (the other IB metal) into the palladium catalyst results in isomerization of the allyl alcohol to propionaldehyde as well as increased combustion of the allyl alcohol. The addition of $H_3PO_4$ increases the formation of propionic acid and propionaldehyde. These observations are evident from Examples 3, 4, 5 and 6.

EXAMPLE 3

Example 1 was repeated using a catalyst containing 1.25% palladium and 0.5% gold supported on alumina; a reactor feed of 14.5 mole percent allyl alcohol, 15.5 mole percent steam and 70 mole percent air; and a contact time of 1.1 seconds. The reaction temperature could not be controlled, rising to 300° C. from a preset temperature of 193° C. The products were:

|  | g./l. cat./hr. |
|---|---|
| Acrylic Acid | 1.8 |
| Acrolein | 69.0 |
| Propionaldehyde | 20.0 |
| Propionic Acid | 2.1 |
| Acetic Acid | 0.7 |
| Carbon Dioxide | 29.0 |

These results showed that the conversion of allyl alcohol was 14.9%. The gold containing catalyst favored the combustion of allyl alcohol as indicated by the increase in $CO_2$ and also increased the rate of isomerization of allyl alcohol to propionaldehyde from 1.7 g./l. cat./hour in Example 1 to 20 g./l. cat./hour.

EXAMPLE 4

Example 1 was repeated using a catalyst containing 1.35% Pd and 0.67% Au on silica, a vapor feed of 11.9 mole percent allyl alcohol, 15.7 mole percent steam and 72.4 mole percent air, a reaction temperature of 207° C. and a 1.1 second contact time. The conversion was 17.6%. Carbon dioxide and propionaldehyde were produced at 30.2 and 14.5 g./l. cat./hour, respectively.

EXAMPLE 5

Example 1 was repeated using a catalyst containing 0.84% Pd, 1.68% Au and 16% $H_3PO_4$ supported on silica and a reaction temperature of 232° C. The vapor feed was obtained by bubbling air through an aqueous solution containing 72.9% allyl alcohol and 27.1% water heated at 70° C. at a rate of 360 cc/minute. The conversion was 10%. Carbon dioxide was formed at a rate of 17.9 g./l. cat./hour. Propionaldehyde and propionic acid were formed at a rate of 18.3 and 13.9 g./l. cat./hour, respectively.

EXAMPLE 6

Example 1 was repeated except that the catalyst was 2% Pd supported on alumina. The reactor feed consisting of 1.44% allyl alcohol vapor, 9.26% steam and 89.3% air was passed through the catalyst at 161° C. and 1.5 second contact time. Carbon dioxide was formed at the rate of 114 g./l. cat./hour amounting to 93.2% combustion of the allyl alcohol feed.

EXAMPLE 7

Step 1 — 30 ml of a catalyst containing 1.3% Pd, 0.6% Au and 3% potassium acetate supported on ⅛ in. silica extrudates having a surface area of 100 m²/g was placed into a 30 ml stainless steel reactor provided with a thermocouple well. The reactor was heated at 160° C. A gaseous feed of 40% propylene, 6% $O_2$, 50% steam and 4% acetic acid was passed through the heated catalyst at a pressure of 5 atmospheres and a contact time of 14 seconds. The reaction mixture leaving the reactor in the gas phase was cooled to 20° C. under pressure and collected in a separator as a two-phase liquid. The upper phase was separated as allyl acetate. The yield of allyl acetate was 94% based on the propylene reacted and the conversion of acetic acid was 99%. The space time yield was 217 g. of allyl acetate/liter of catalyst/hour.

Step 2 — In a separate reactor, the allyl acetate was hydrolyzed with water at 225° C. and a pressure of 5 atmospheres. The mole ratio of allyl acetate to water was 1:5. The hydrolysis mixture was distilled giving an azeotropic fraction boiling at 88.2° C. consisting of 72.9 weight percent allyl alcohol and 27.1 weight percent water. The bottoms, consisting of aqueous acetic acid, was adjusted to give a mole ratio of water to acetic acid of 12.5:1. The acetic acid water mixture was then recycled to reactor 1 (Step 1) for use in the oxidation of propylene to allyl acetate.

Step 3 — The allyl alcohol azeotrope fraction was diluted with water to give a mole ratio of water to allyl alcohol of 9:1. This mixture was vaporized, mixed with air and fed into a reactor containing 31 g. of a catalyst containing 2% palladium and 0.5% copper supported on alumina, at a temperature of 155° C. The contact time was 1.5 seconds. The exiting reaction mixture was bubbled through two 40 ml. water traps (0° C.) which were connected in series. The aqueous solution collected over a one hour period showed that the conversion of allyl alcohol was 80% and the selectivity to the acroyl moiety was 83%.

EXAMPLE 8

A Pyrex glass reactor (12 × 2.5 cm O.D.) provided with a thermowell, was packed with 31 g. (30 ml bulk volume) of a catalyst containing 2 wt. % palladium and 0.5 wt. % copper supported on alumina. The reactor was heated in an oil bath at about 152° C. A gaseous stream consisting of 3.4 volume % acrolein, 14.8% oxygen, 22.9% steam and 58.5% nitrogen was passed through the heated catalyst at a rate such that the superficial contact time was about 4.9 seconds. The reaction mixture was then passed through two water scrubbers connected in series and held at 0° C. The aqueous solutions collected were combined and analyzed by gas liquid chromatography and alkaline titration. The analyses indicated that acrolein was oxidized to acrylic acid in 90.6% selectivity at 21% conversion with a production rate of 22 g./l. cat./hr.

EXAMPLE 9

Example 8 was repeated except that the catalyst contained 2% palladium and 0.5% silver supported on alumina and was heated at about 168° C. The feed consisted of 4.8% acrolein, 23.3% steam and 71.9% air and was passed through the heated catalyst at a superficial contact time of about 1.8 seconds. The analysis disclosed formation of acrylic acid at the rate 26.4 g./l. cat./hr. with a conversion of 14.5% and 95% selectivity.

EXAMPLE 10

Example 8 was repeated except that the catalyst contained 1.3% palladium and 0.6% gold supported on alumina and was heated at 189° C. The feed consisted of 4.3% acrolein, 18.9% steam and 76.8% air and was passed through the heated catalyst at a superficial contact time of about 1.8 seconds. The analysis indicated that acrylic acid was obtained in 19.3% selectivity at 15.5% acrolein conversion with carbon dioxide as the major product.

EXAMPLE 11

Example 8 was repeated except that the catalyst contained 2% palladium supported on alumina and was heated at 178° C. The analysis showed that carbon dioxide was the major product with trace amounts of acrylic and acetic acids being formed.

EXAMPLE 12

Example 8 was repeated except that the catalyst contained 1.2% palladium and 2.4% gold. The feed consisted of 4.1% acrolein, 22.7% steam and 76.2% air and was passed through the catalyst at about 237° C. and 2 seconds superficial contact time. Carbon dioxide was the major product. Acrylic acid was obtained at the rate of 10.8 g./l. cat./hr. at 1.4% selectivity and 83% acrolein conversion.

Various changes and modifications can be made in the process of this invention without departing from the spirit and scope thereof. The various embodiments disclosed herein were for the purpose of further illustrating the invention but were not intended to limit it.

I claim:

1. A vapor phase process which comprises oxidizing acrolein by reacting the acrolein with an oxygen containing gas at a temperature of 125°–320° C in the presence of a supported two-metal catalyst wherein one metal is palladium and the second metal is copper or silver, and recovering acrylic acid.

2. The process of claim 1 wherein the catalyst metals are palladium and copper and said temperature is 150°–200° C.

3. The process of claim 1 wherein said metals are palladium and silver and said temperature is 150°–200° C.

4. The process of claim 1 wherein the superficial contact time with said catalyst is from 0.1 to 10 seconds.

5. The process of claim 1 wherein said palladium is about 0.01 to 5 weight percent of said supported catalyst, said copper or silver is 0.001 to 10 weight percent of said supported catalyst, and the weight ratio of copper or silver to palladium is 0.1 to 2.0.

6. The process of claim 5 wherein said palladium is about 0.1 to 2 weight percent, said copper or silver is about 0.05 to 3 weight percent, and said weight ratio is 0.5 to 1.5.

7. The process of claim 1, also comprising supplying water to the reaction in a molar ratio of water to acrolein of about 1:1 to 20:1.

8. The process of claim 1, wherein the reaction feed comprises an azeotrope of water and acrolein.

* * * * *